United States Patent [19]
Pui et al.

[11] Patent Number: 5,973,904
[45] Date of Patent: Oct. 26, 1999

[54] PARTICLE CHARGING APPARATUS AND METHOD OF CHARGING PARTICLES

[75] Inventors: David Y. H. Pui, Plymouth; Da-Ren Chen, Lauderdale, both of Minn.

[73] Assignee: Regents of the University of Minnesota

[21] Appl. No.: 08/949,154

[22] Filed: Oct. 10, 1997

[51] Int. Cl.⁶ .................................................... B05B 5/053
[52] U.S. Cl. .......................................... 361/225; 361/226
[58] Field of Search ..................................... 361/225–229, 361/230, 235; 250/324–326

[56] References Cited

U.S. PATENT DOCUMENTS

| 4,265,641 | 5/1981 | Natarajan . |
| 4,414,603 | 11/1983 | Masuda . |
| 5,247,842 | 9/1993 | Kaufman et al. . |
| 5,475,228 | 12/1995 | Palathingal . |

FOREIGN PATENT DOCUMENTS

WO 93/07465   4/1993   WIPO .

OTHER PUBLICATIONS

Adachi et al., "Unipolar And Bipolar Diffusion Charging of Ultrafine Aerosol Particles," *J. Aerosol Sci.*, 16(2), 109–123 (1985).

Adachi et al., "High–efficiency unipolar aerosol charger using a radioactive alpha source," *Aerosol Science, Idustry Health and Environment*, pp. 439–441, (Masuda and Takahashi, eds.), Pergamon Press, NY (1990).

Büscher et al., "Performance of a unipolar 'square wave' diffusion charger with variable nt–product," *J. Aerosol Sci.*, 25(4), 651–663 (1994).

Chen et al., "Design and Evaluation of a Nanometer Aerosol Differential Mobility Analyzer (Nano–DMA)," *J. Aerosol Sci.*, 29(5/6), 497–509 (1998).

Chen et al., "Electrospraying of Conducting Liquids for Monodisperse Aerosol Generation in the 4nm To 1.8 $\mu$m Diameter Range," *J. Aerosol Sci.*, 26(6), 963–977 (1995).

Chen et al., "Experimental Investigation of Scaling Laws for Electrospraying: Dielectric Constant Effect," *Aerosol Sci. Tech.*, 27, 367–380 (1997).

Fuchs, "On the Stationary Charge Distribution on Aerosol Particles in a Bipolar Ionic Atmosphere," *Geodis:Pura. Appl.* 56, 185–193 (1963).

Hoppel et al., "The Nonequilibrium Character of the Aerosol Charge Distributions Produced by Neutralizers," *Aerosol Sci. & Technol.*, 12, 471–496 (1990).

(List continued on next page.)

*Primary Examiner*—Fritz Fleming
*Attorney, Agent, or Firm*—Mueting, Raasch & Gebhardt, P.A.

[57] ABSTRACT

A method for charging of aerosol particles includes providing a charger housing having a longitudinal axis extending between an inlet and an outlet of the charger housing with a stream of aerosol particles flowing parallel to the longitudinal axis from the inlet to the outlet. A confined electric field is created within the housing parallel to the longitudinal axis for directing a stream of unipolar ions to flow parallel to the longitudinal axis of the charger housing towards the outlet for use in charging the stream of aerosol particles. To further reduce charged particle loss within the charger housing, a clean sheath may be created between the stream of aerosol particles and the charger housing, an outlet electric field may be created proximate the outlet of the charger housing such that charged particles are forced towards the longitudinal axis, and/or the stream of aerosol is contracted proximate the outlet of the charger housing forcing the charged particles toward the longitudinal axis. Apparatus for carrying out the method is also described.

33 Claims, 9 Drawing Sheets

OTHER PUBLICATIONS

Lui et al., "On unipolar diffusion charging of aerosol particles in the continuum regime," *J. Colloid Interface Sci.,* 58, 142–149 (1977).

Pui et al., "Nanometer Particles: A New Frontier For Multidisciplinary Research," *J. Aerosol Sci.,* 28(4), 539–544 (1997).

Pui et al., "Unipolar Diffusion Charging Ultrafine Aerosols," *Aerosol Sci. Techn.,* 8, 173–187 (1988).

Romay et al., "Unipolar Diffusion Charging of Aerosol Particles at Low Pressure," *Aerosol Sci. Techn.,* 15, 60–68 (1991).

Romay et al., On the combination coefficient of positive ions with ultrafine neutral particles in the transition and free–molecule regimes, *Aerosol Sci. Techn.,* 17, 134–147 (1992).

Romay et al., "Free electron charging of ultrafine aerosol particles," *J. Aerosol Sci.,* 23(7), 679–692 (1992).

Wiedensohler et al., "A novel unipolar charger for ultrafine aerosol particles with minimal particle losses," *J. Aerosol Sci.,* 25(4), 639–650 (1994).

PARTICLE CHARGING APPARATUS AND METHOD OF CHARGING PARTICLES

STATEMENT OF GOVERNMENT RIGHTS

The present invention was made with government support from the National Science Foundation under Grant No. CTS-9304152. The Government has certain rights in this invention.

FIELD OF THE INVENTION

The present invention relates to the unipolar charging of particles. More particularly, the present invention pertains to apparatus and methods for electrically charging particles by collision, e.g., such as with unipolar ions.

BACKGROUND OF THE INVENTION

Various aerosol chargers are currently available to impart electric charge, of either positive or negative polarity, on airborne particles. Charged aerosol particles can be deflected in an electric field. The electric force on submicron particles can be more than a million times greater than other forces, e.g., gravitational force. Consequently, electric charging of aerosol particles followed by electric field manipulation, is a principal technique used in the measurement and control of submicron particles.

Such measurement and control of submicron particles is beneficial with regard to many applications. For example, such applications include the control of fly ash from power plants by electrostatic precipitation and in the measurement of aerosol size distributions. Further, aerosol technology has been used for the synthesis of new materials with particular interest in production of ultrafine particles such as for applications including photoimaging, magnetic tapes, filtration and electro-optical applications. To develop such technologies, techniques are needed to measure the particle size distributions, to classify the particles into monodisperse fractions, and to recover the particles from the aerosol form. In addition, particulate contaminants are major causes for yield losses in semiconductor device fabrication, particularly for submicron features. Particles smaller than the feature sizes must be controlled and measured to be able to address such contamination problems. The principle of charging particles and manipulating such particles in an electric field are used in the development of such technologies and for arriving at solutions to address such problems.

Airborne particles can be charged by various methods, for example such methods include contact (triboelectric) charging, spray charging, photoelectric charging, or by gaseous ions. Charging by gaseous ions is a preferred method for aerosol charging because such charging by gaseous ions is a repeatable process and is theoretically predictable.

Charging by gaseous ions involves producing gaseous ions of one polarity (unipolar) or of both polarities (bipolar), and allowing the ions to collide with aerosol particles due to their random thermal motion. In other words, unipolar charging is the charging of particles in a gaseous medium containing ions of one polarity and bipolar charging is the charging of particles in a gaseous medium containing ions of both polarities.

Various unipolar aerosol chargers are available and/or have been described. One currently available charger is the unipolar aerosol charger used in the Electrical Aerosol Analyzer available under the trade designation TSI Model 3030 from TSI, Inc. (MN). This charger is described in the article by Pui, et al., entitled "Unipolar Diffusion Charging of Ultrafine Aerosols" *Aerosol Science and Technology,* 8: 173–187 (1988). This charger involves passing ions in a stream perpendicular to the aerosol particle stream passing through the device. As the aerosol particle stream passes through the stream of unipolar ions, the aerosol particles are charged via collisions of the aerosol particles with the unipolar ions. The ion stream is directed with an electric field perpendicular to the aerosol stream.

Another similarly configured particle charger with an ion stream perpendicular to the aerosol stream is described in an article by Buscher, et al., entitled "Performance of a Unipolar 'Square Wave' Diffusion Charger With Variable nt-Product," *J.Aerosol.Sci,* Vol. 25, No. 4, pp. 651–663 (1994). This charger uses a chopping electric field created using a square wave voltage across the charging zone to alleviate particle losses.

Yet another charger is described in an article by Romay et al., entitled "Unipolar Diffusion Charging of Aerosol Particles at Low Pressure," *Aerosol Science and Technology,* 15: 60–68 (1991). This charger includes an elongated tube having a voltage applied between two metallic screen electrodes. One of the screens is positioned at an aerosol inlet and the other at an exit of the charger. A radioactive source is positioned close to the inlet such that when a voltage is applied, bipolar ions fill the volume by the inlet screen and unipolar ions fill the region between the source and the exit screen electrode. The unipolar ions filling the region charge the particles with such charged particles exiting through the exit screen. An electric field is created in the ion containing region; however, unlike the previously described chargers above, the electric field is not perpendicular to and does not direct the ions perpendicularly relative to the aerosol stream passing through the charger. The electric field of this charger includes an electric field that includes fringes directed to the wall of the charger. Various other chargers have also been described. For example, another unipolar charger is described in the article by Wiedensohler et al., entitled "A novel unipolar charger for ultrafine aerosol particles with minimal particle losses," *J.Aerosol.Sci* Vol. 25, No. 4, pp. 639–650 (1994).

Charging of the aerosol particles becomes increasingly difficult as particle size gets smaller because the collision cross section of the particles becomes small relative to the mean-free-path of the ions. In the nanometer particle size range, e.g., 2 nm to 100 nm, such nanometer particles seldom carry more than a few elementary units of charge. For example, below 10 nm, an increasing fraction of the particles are not charged, i.e., they are electrically neutral, leaving only a small fraction of the nanometer particles being charged. Additionally, the small fraction of charged particles often are lost in the charger due to the high electric mobility of such charged nanometer particles. The currently available chargers or described chargers are not adequate to charge submicron particles, particularly not adequate for charging nanometer particles. Such chargers have charged particle losses that are undesirably large leading to only a small fraction of charged particles being allowed to exit the charger.

For example, most of the existing chargers involve passing an ion stream perpendicularly to the aerosol particle stream flowing through the charger. The charged particles resulting from collisions with the ions in the ion stream are deflected in the same direction as the flow of the ion stream. Such deflection results in significant charged particle loss due to the charged particles being deflected and captured on surfaces of the charger.

Further, Brownian diffusion causes the aerosol stream to spread as it passes through existing chargers further causing charged particles in the stream to be in close contact with charger structure. Contact with such charger structure also results in losses of charged particles.

Yet further, many existing chargers have structure or obstructions therein lying in the path of the flow of the charged particles through the apparatus that cause charged particle losses. For example, charged particle streams flowing through chargers wherein the charged particles must exit the charger by passing through an obstruction, e.g., such as a screen electrode at an outlet of the charger as described above, results in charged particle losses.

The importance of charged particles, particularly nanometer particles, for technological applications is known as described above. For example, nanostructured materials composed of nanometer particles often possess significantly enhanced mechanical, optical, electrical/magnetic properties, which are desirable for advanced engineering applications. Many of the advanced applications, e.g., tunable lasers, require depositing uniform size nanometer particles in layers. The uniformity requirement is quite stringent, often within 5% of the mean size. The particles can be made uniform by passing through a differential mobility analyzer (DMA) which classifies the airborne particles in a condenser according to the particles electrical mobility. A narrow slit is used to extract particles with nearly the same mobility. The DMA is therefore equivalent to that of a band pass filter with a narrow mobility window. By connecting a particle counter downstream of the DMA, the system can be used to measure particle size distributions which can be inferred from the electric mobility distributions.

The difficulty involved in DMA classification and measurement for particles, and in particular nanometer particles, is that only a small fraction of particles introduced into a charger are actually charged and exit the charger. A large fraction of the charged particles is typically lost within the charger, resulting in a small extrinsic charging efficiency.

For this reason and other reasons, there is a need in the art to provide high charging efficiency and low loss characteristics, i.e, a high throughput charger which overcomes the disadvantages as described above. The present invention addresses such needs and alleviates such problems described above, and other problems as will become apparent to one skilled in the art from the detailed description below.

SUMMARY OF THE INVENTION

A method for unipolar charging of aerosol particles according to the present invention includes providing a charger housing having a longitudinal axis extending between an inlet and an outlet of the charger housing with a stream of aerosol particles flowing parallel to the longitudinal axis from the inlet to the outlet. A confined electric field is created within the housing parallel to the longitudinal axis for directing a stream of unipolar ions to flow parallel to the longitudinal axis of the charger housing towards the outlet for use in charging the stream of aerosol particles.

In one embodiment of the method, a clean sheath is created between the stream of aerosol particles and the charger housing. In another embodiment of the method, the method further includes creating an outlet electric field proximate the outlet of the charger housing. The outlet electric field has a direction generally opposite of the direction of the confined electric field such that charged particles are forced towards the longitudinal axis. In another embodiment of the method, the method further includes sizing the charger housing such that the stream of aerosol is contracted proximate the outlet of the charger housing such that charged particles of the stream are forced towards the longitudinal axis.

In another method according to the present invention, the method includes providing a stream of uniformly sized aerosol particles in a charging apparatus. The uniformly sized particles have a mean diameter in the range of about 3 nanometers or greater. The method further includes providing a stream of unipolar ions in the charging apparatus for collision with the stream of uniformly sized aerosol particles. A charged fraction of the stream of uniformly sized aerosol particles exiting the charging apparatus is about 0.2 or greater.

In one embodiment of the method, the stream of uniformly sized aerosol particles have a mean diameter in the range of about 4 nanometers or greater with the charged fraction of the stream of uniformly sized aerosol particles exiting the charging apparatus being about 0.4 or greater.

An aerosol particle charging apparatus according to the present invention for use in charging a stream of aerosol particles includes an elongated charger housing having a longitudinal axis extending between an inlet and an outlet defined therein. The inlet is for receiving the stream of aerosol particles and the outlet is for allowing the stream of aerosol particles to exit the charger housing. The apparatus further includes an electrode configuration operable to create a confined uniform electric field within the housing parallel to the longitudinal axis for use in directing a stream of unipolar ions to flow parallel to the longitudinal axis of the charger housing towards the outlet.

In one embodiment of the charging apparatus, the apparatus further structure for creating a clean sheath between the stream of aerosol particles and the charger housing. In another embodiment of the charging apparatus, the apparatus includes structure such that the stream of aerosol particles is contracted proximate the outlet of the charger housing forcing the stream of aerosol particles towards the longitudinal axis of the charging device. In another embodiment of the invention, the apparatus further includes an electrode proximate the outlet of the charger housing operable to create an outlet electric field in a direction generally opposite of the direction of the confined electric field such that charged particles of the stream of aerosol particles are forced towards the longitudinal axis.

Another aerosol particle charging apparatus for use in charging a stream of aerosol particles is also described. The apparatus includes an elongated charger housing having a longitudinal axis extending between an inlet and an outlet defined therein. The inlet is for receiving the stream of aerosol particles and the outlet is for allowing the stream of aerosol particles to exit the charger housing. The charging apparatus further includes a plurality of corona discharge elements positioned along the longitudinal axis for providing free electrons and/or ions into a charging zone defined by the charger housing and an electrode configuration operable to create a confined uniform electric field within the housing parallel to the longitudinal axis.

BRIEF DESCRIPTION OF THE DRAWINGS

FIGS. 2A, 2B, and 2C are end views and a cross-section view respectively of the particle charging apparatus of FIG.

1; the cross-section view taken through one of the electrodes located towards the middle of the particle charging apparatus of FIG. 1.

DETAILED DESCRIPTION OF THE EMBODIMENTS

The present invention shall be described with reference to FIGS. 1–6. Thereafter, results with regard to one embodiment of the present invention shall be described with reference to FIGS. 7–9. It will be apparent to one skilled in the art that elements from one embodiment of the present invention may be used in combination with elements of one or more of the other embodiments and that the present invention is not limited to the specific illustrative embodiments described herein but only as described in the accompanying claims.

The present invention is directed to apparatus and methods for charging aerosol particles. Although the present invention is advantageous in the charging and provision of charged submicron particles (i.e., particles having a nominal diameter of less than about 1 micron), the advantages are even greater for the charging and provision of charged nanometer particles (i.e., particles having a nominal diameter of less than about 100 nanometers). Particularly, as will become apparent from the description to follow, the present invention provides yet even greater advantages in the charging and provision of charged nanometer particles having a nominal diameter of less than about 20 nanometers. Many types of particles may be charged according to the present invention (e.g., polystyrene, silver, biological material, etc.), and the present invention is not limited to any particular type of aerosol particles.

Figure 2A:
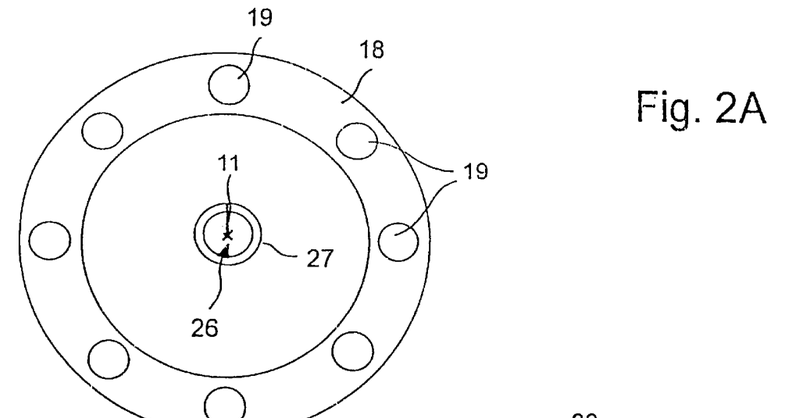
Figures 2B, 2C:
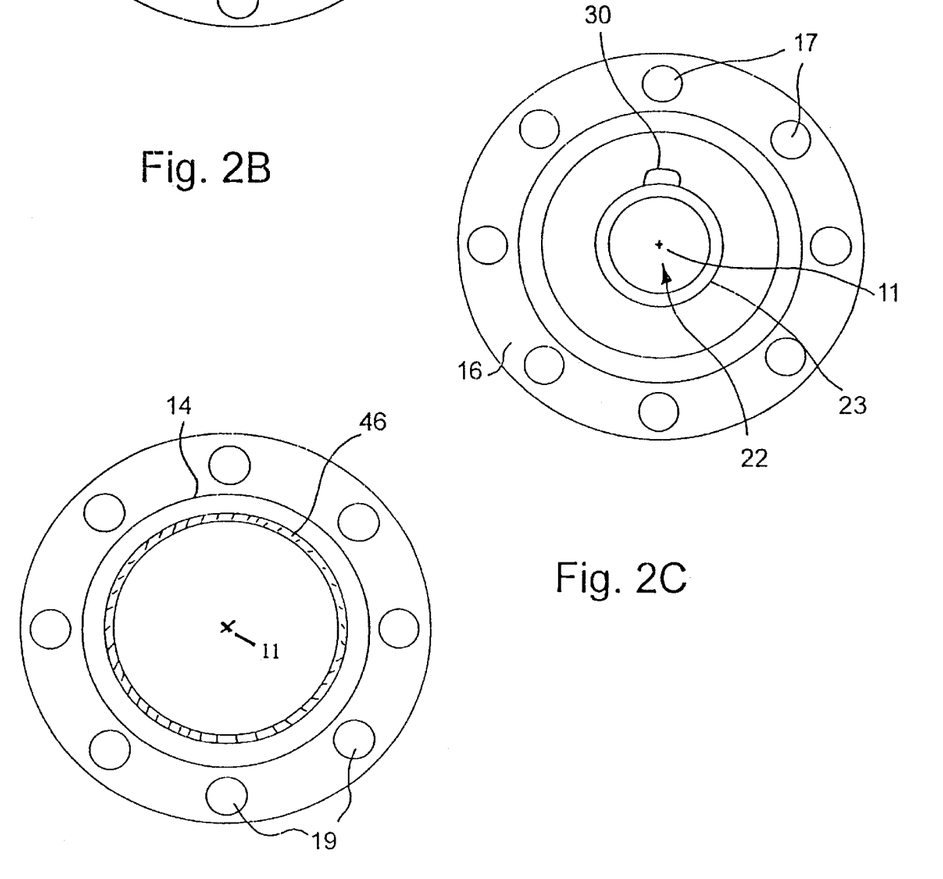
Figure 3:
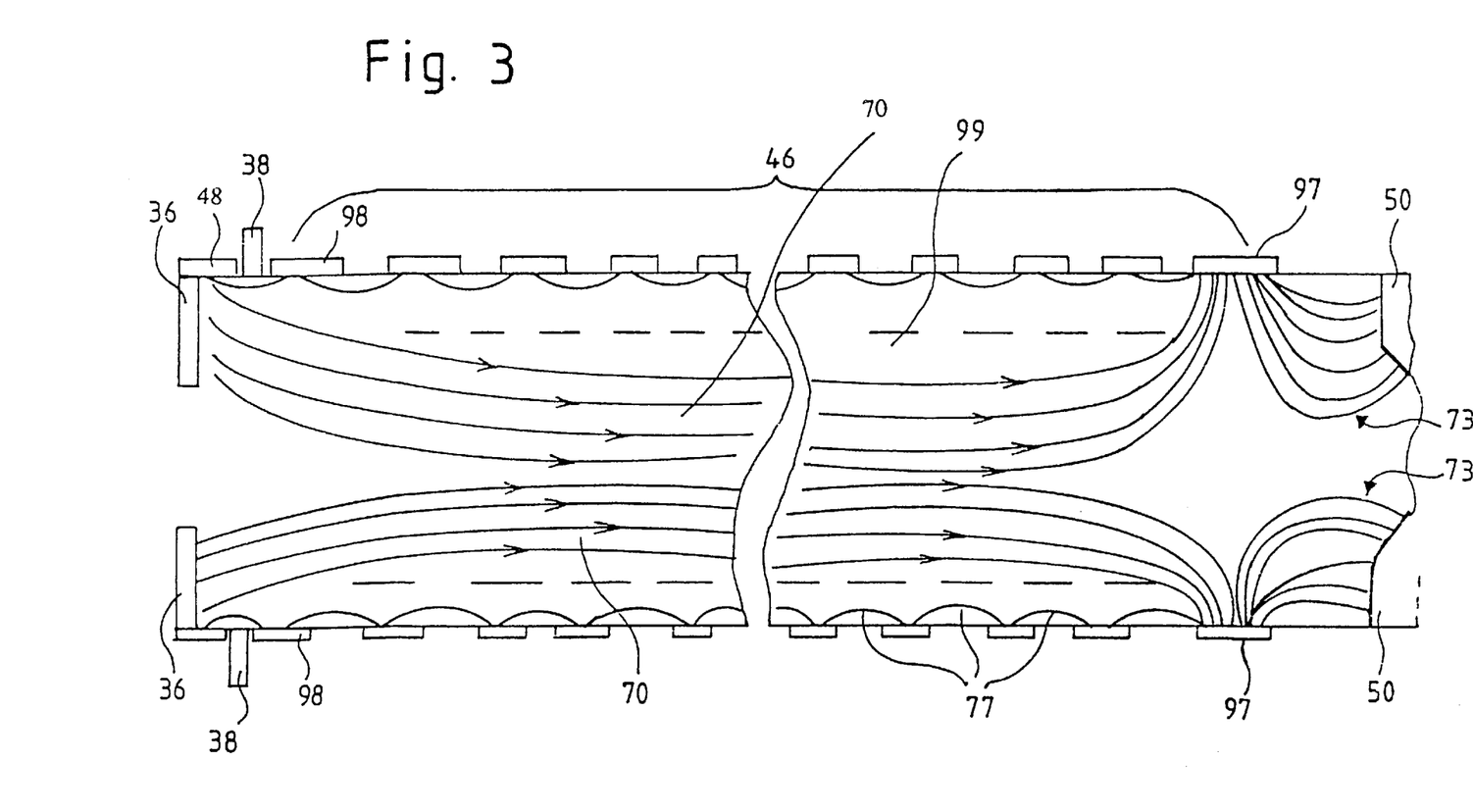
FIG. 3 is a diagram showing the electric field set up when the electrodes are operational in the particle charging apparatus of FIG. 1.

The unipolar particle charging apparatus 10 according to the present invention shall be generally described with reference to FIGS. 1–3. The charging apparatus 10 includes an elongated charger housing 12 having a longitudinal axis 11 extending therethrough. The charger housing 12 includes a generally tubular housing member 14 lying along the longitudinal axis 11 which defines at least a portion of a charging zone or volume 13. The charger housing 12 further includes a first annular end member 16 and a second annular end member 18. The first annular end member 16 is connected and sealed to one end of the tubular housing member 14 using fasteners 17 and seal element 72 and the second annular end member 18 is connected to the other end of the tubular housing member 14 with fasteners 19 and seals 73. It will be apparent to one skilled in the art that any sort of connection elements may be used in the construction of the charger housing and that the charger housing may be constructed as a single element or any other number of elements or members.

Further, the housing 12 may be constructed of any number of nonconducting materials such as plexiglass, ceramic, etc. If the housing is formed of ceramic material, the charger 10 can then be baked prior to charging experiments. Such baking together with the use of high purity gases, will allow ions of known species to interact with the aerosol particles. Results from such experiments can be used to test existing theories on charging efficiency.

An inlet 22 is defined in the first end member 16 of the charger housing 12 for receiving a stream 20 of aerosol particles (e.g., uniformly sized neutral particles) and an outlet 26 is defined in the second end member 18 of the charger housing 12 for allowing the exit of a stream 24 of aerosol particles. The charger housing 12 defines a substantially obstruction free charging zone extending from the inlet 22 to the outlet 26. In other words, the flow of aerosol particles 20 has an unobstructed path along the longitudinal axis of the charging apparatus 10. For example, there are no screens, electrodes, or any other obstructions which the stream of aerosol is required to pass through. By providing an obstruction free path from the inlet to the outlet along the longitudinal axis, the possibility of particle loss on such obstructions is minimized.

The inlet 22 is defined by an annular inlet member 23 that is concentric with the first end member 16 about the longitudinal axis 11. A portion of the annular inlet member 23 extends beyond the opening 25 defined in the first end member 16 to facilitate connection of the apparatus 10 to equipment providing the stream 20 of aerosol particles. A portion 27 of the annular inlet member 23 extends to the interior of the first end member 16 for defining an annular cavity 34 with a portion of the first end 16 and an annular metal screen 36. The cavity 34 is for receiving air or a gas 28 through air inlet 30 defined in the first end 16. The portion 27 of the annular inlet member 23 is tapered to promote movement of the air or gas 28 in the cavity 34 towards the metal screen 36 (e.g., a low porosity screen, sintered metal, perforated metal, or the like) such that an annular clean air sheath 52 is provided between the stream of aerosol particles 50 in the charging zone 13 and the charger housing 12. In other words, the annular air sheath surrounds the stream of aerosol particles 50 in the charging zone 13.

One skilled in the art will recognize that due to Brownian diffusion the stream of aerosol particles 50 spread as they move through the charging zone 13. The aerosol particles take somewhat of a Gaussian distribution from the longitudinal axis to the charger housing 12. The clean sheath 52 which surrounds the stream 50 minimizes the loss of particles to the inner surface 47 of the charger housing 12. The clean sheath 52 flows parallel to the longitudinal axis 11 from the metal screen 36 to the outlet 26. The clean sheath 52 may be created using any inert gas (e.g. nitrogen, helium, argon), particle free air, or the like. The clean air sheath 52 is provided by providing a flow of air or gas 28 that is in the range of about 2 to about 5 times the flow of the neutral aerosol stream 20 into the inlet 22; preferably about 3 times the flow of the aerosol stream 20.

The outlet 26 is defined by an annular outlet member 27 that is concentric with the second end member 18 about the longitudinal axis 11. A portion of the annular outlet member 27 extends beyond the opening 35 of the first end member 18 to facilitate connection of the apparatus 10 to equipment to which the stream 24 of charged aerosol particles is provided. The annular inlet member 23 and the annular outlet member 27 are sized to provide an abrupt contraction of the aerosol stream 50 in the charging zone 13 proximate the outlet 26 of the charger housing 12 such that the charged particles are forced towards the longitudinal axis 11 of the charging apparatus 10, or in other words are forced to the center of the outlet 26, i.e, exit. As will be described further below, an annular electrode 61 proximate the outlet 26 of the charger housing 12 is utilized to create an outlet electric field having a direction that is generally opposite to the direction of a confined uniform electrical field created in a core region of the charging zone about the longitudinal axis 11 such that charged particles of the stream 50 of aerosol particles in the charging zone 13 are forced towards the longitudinal axis as such particles near the outlet 26. These two techniques of forcing the charged particles to the center of the exit port or outlet 26 minimize the loss of charged particles.

The flow field contraction force to force the charged particles towards the longitudinal axis (i.e., the center of the outlet 26) is achieved by selecting appropriate sizing for the inlet 22 and outlet 26. The diameter of the outlet 22 is preferably in the range of about 0.3 to about 0.7 times the diameter of the inlet 22; more preferably the diameter of the outlet 26 is about 0.5 times the diameter of the inlet 22.

In addition, the size of the tubular housing member 14 is selected such that the Brownian diffusion effects on the stream of aerosol particles 50 in the charging zone 13 are minimized. In other words, the size of tubular housing member 14 is selected so that the spread of particles does not reach the wall and result in particle loss. Preferably, the diameter of the tubular housing member 14 is in the range of about 1.5 to about 3 times the diameter of the inlet 22; more preferably the diameter of the tubular housing member 14 is about 2 times the diameter of the inlet 22.

The apparatus 10 further includes an ion source 38 for use in providing a stream of unipolar ions to the charging zone 13. In this particular embodiment, the ion source 38 is a radioactive source used to produce bipolar ions in an indented annular slot 63 in tubular housing member 14. For example, the radioactive source may be polonium-210, carbon-14, Kr-85, Ni-63, Am-241, or any other known and suitable radioactive source for providing bipolar ions.

The indented annular slot 63 in tubular housing member 14 is positioned in proximity to the inlet 22 of the charger housing 12 along the inner surface 47 of the tubular housing member 14. A ring electrode 48 is positioned between the inlet 22 of the charger housing 12 and the ion source 38. Electrodes 46 and 48 are used to set up the confined uniform electric field as described further below. The ring electrode 48 is electrically connected to the annular metal screen 36. With the electrode 48 grounded as further described below, and the electrodes 46 being operable, the confined uniform electric field causes ions of one polarity to be pushed towards the electrode 48/screen 36 in a relatively short section of the charging zone 13 compared to the remaining portion of the charging zone 13. Such removal of ions of one polarity allows a stream of unipolar ions to be directed to flow into the charging zone 13 by the confined electric field to collide with the parallel stream of aerosol particles flowing from the inlet 22 to the outlet 26 causing aerosol particles to be charged.

It will be apparent to one skilled in the art that the negative or positive nature of the voltages applied will cause the unipolar ions in the charging zone 13 to be either positive or negative. In this particular illustration, the voltage applied is −x volts and as such positive ions are supplied to the charging zone 13. The reversal of the voltages as applied including the reversal of the ramped nature of such voltages throughout the description herein is contemplated within the scope of the present invention to achieve both positive and negative charging of particles. The particular voltages used for illustration herein are not to be construed as being unduly limiting to the present invention as the present invention is limited only in accordance with accompanying claims.

It will be apparent to one skilled in the art that the ion source 38 may be a corona discharge electrode, e.g., a ring of needles or a sharp inner-edge ring with an applied voltage. Use of a corona discharge electrode would allow the charger to be operated without the use of a radioactive source.

As described in the Background of the Invention section herein, many of the existing/described chargers involve passing the ion stream perpendicular to the stream of aerosol particles to allow for collision and thus charging of particles. In the apparatus 10 of the present invention, the stream of aerosol particles 50 in the charging zone flows parallel to the stream of ions and a confined uniform electric field in a flow direction from the inlet 22 to the outlet 26 along and parallel to the longitudinal axis 11. This allows the present charger to minimize losses conventionally due to deflection of charged particles in the direction of the ion stream.

Generally, the confined uniform electric field which is substantially parallel to the flow of the aerosol particle stream and the unipolar ion stream is generated using a drifting tube electrode configuration 44. The confined uniform electric field 70 is generally shown in FIG. 3 with the field being set up by utilizing insulated ring electrodes 46 and ring electrode 48 distributed along the longitudinal axis 11. The ring electrodes are preferably placed equal distances apart. Any suitable number of rings electrodes may be used to create the field, preferably 5 or more ring electrodes. Voltages ramped in level from the first ring electrode 97 to the last ring electrode 98 of the ring electrodes 46 lying along the longitudinal axis 11 are applied to the electrodes 46 by one or more power sources generally represented by the reference arrow 40 pointing out the various voltages being applied. In other words, as shown in FIG. 1, the first electrode 97 of the ring electrodes 46 has an applied voltage of −y volts and the last electrode of the ring electrodes 46 has an applied voltage of −x volts. The ring electrodes 46 between the first and last electrodes have voltages applied at a level somewhere between −y volts and −x volts in a ramped manner.

With DC voltages applied, this drifting tube electrode configuration allows a confined uniform electric field to be set up parallel to the flow of the aerosol particles and the stream of unipolar ions. When aerosol particles are charged by the unipolar ions, the charged particles tend to speed to the outlet 26 and thus have reduced residence time in the charging zone compared to those that are charged closer to the outlet 26.

The confined uniform electric field 70 is defined as a field which is substantially uniform in a core region 99 about the longitudinal axis 11 in the charging zone 13 with no uncontrolled fringing of the electric field from the core region 99 to the charger housing 12. The confined field 70 is generally parallel to the longitudinal axis 11 and in a direction towards the outlet 26. Controlled fringing between the ring electrodes is shown by reference numeral 77 in FIG. 3. This fringing does not run from the core region 99 to the charger housing and is controlled or confined by use of the air sheath. For example, the air sheath can be sized to encompass the maximum possible field fringing of the electrodes 46, e.g., the air sheath width can be set two times the maximum distance the fringing extends into the charging region 13. Such fringing does not exist with the continuous resistor layer configuration described further below with reference to FIG. 5.

Figure 1:
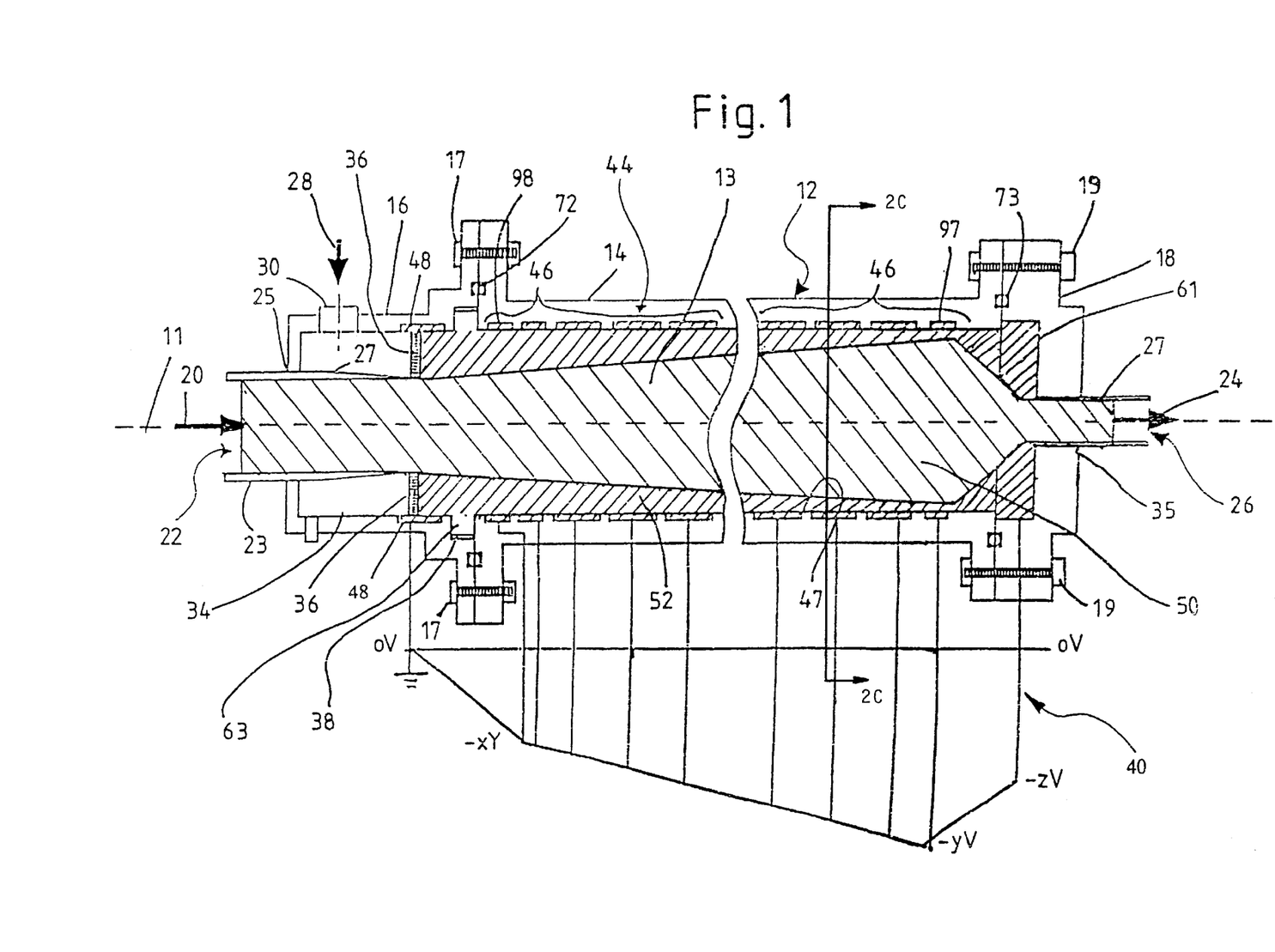
FIG. 1 is a diagrammatical cross-section view of a particle charging in apparatus in accordance with the present invention.

Further shown in FIG. 1 is the application of a voltage level, −z volts, to the annular electrode 61. The voltage level, −z volts, is less negative than the voltage, −y volts, applied to the first ring electrode 97 of the ring electrodes 46. Electrode 61 having such a voltage applied creates an outlet electric field 73, as shown in FIG. 3, that is generally opposite in direction relative to the electric field 70 or in other words the field in this region is reversed relative to the confined electric field 70. As previously mentioned, this field 73 forces charged particles away from the electrode and towards the longitudinal axis 11 by flow contraction forces such that the charged particles are not lost on housing surfaces at the exit of the apparatus 10. As used herein, an electric field that has a direction generally opposite to the confined electric field or reversed relative to the confined electric field is meant to encompass any electric field which applies forces to a particle for moving the particle in a direction different than the movement which would occur with the confined electric field (in the case of smaller particles such as submicron particles) or which would slow the movement occurring under forces of the confined electric field (in the case of larger particles), e.g., move particles in reverse direction, move particles in a generally opposite direction, move particles in a direction away from the outlet as opposed to towards the outlet, slow particles as they near the outlet, etc.

Figure 5:
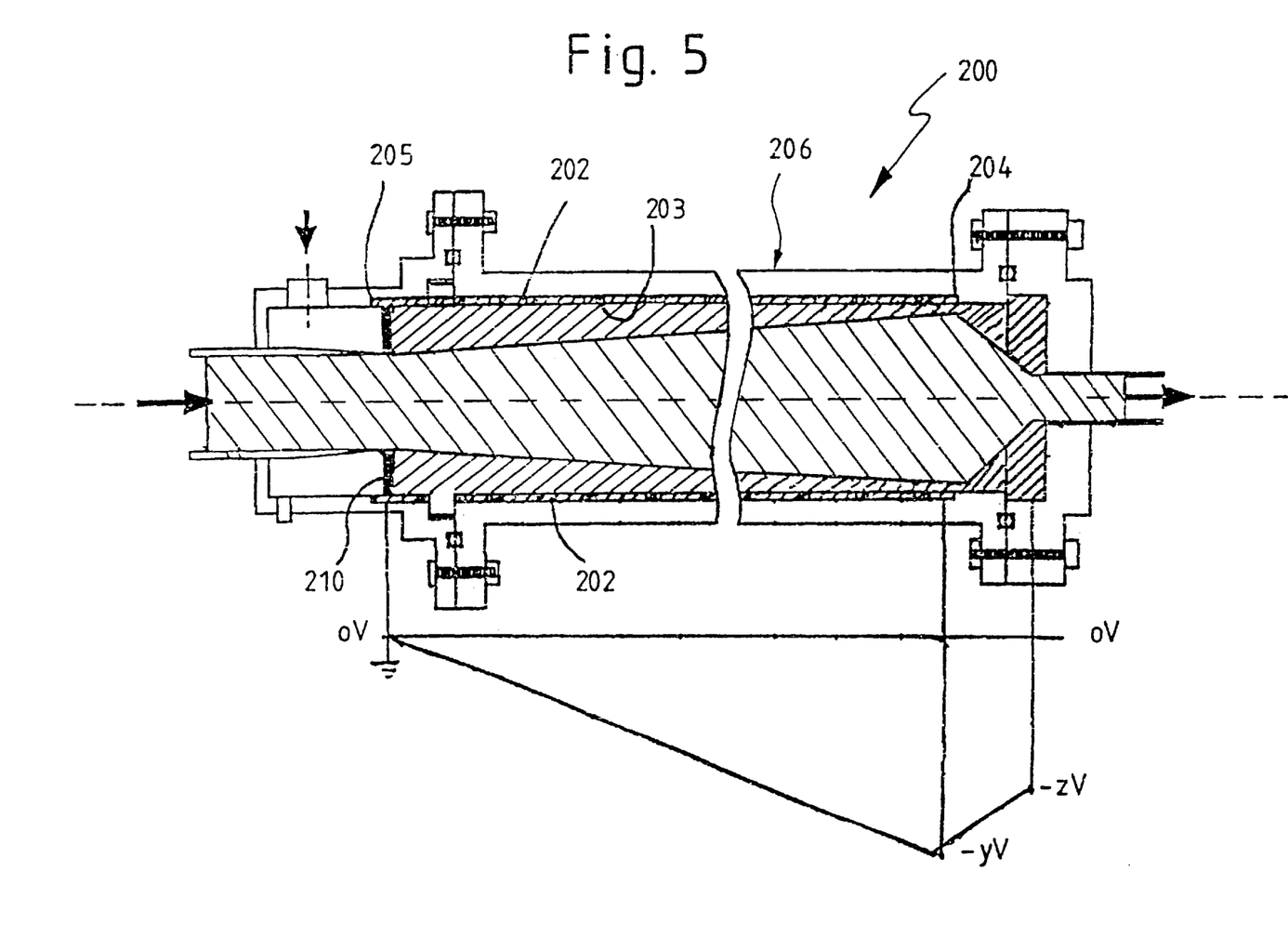
FIG. 5 is a cross-section illustration of an alternate embodiment of the particle charging apparatus of FIG. 1 in accordance with the present invention.

The confined electric field 70 can also be set up using the alternate drifting tube electrode configuration shown in the illustration of FIG. 5. As shown therein, the ring electrodes are replaced by a thick film resistor 202 of uniform thickness on a portion of the nonconducting inner surface 203 of the charger housing 206. The resistor layer 202 extends from a first end 204 to a second end 205 which is connected to the metal screen 210 and grounded. When a voltage is applied to the first end 204 of the resistor layer 202, the voltage ramps (e.g., becomes less negative) along the axial direction towards the second end 205 which is electrically grounded. This electrode configuration also provides a confined uniform electric field parallel to the flow of aerosol particles and unipolar ions.

Figure 4:
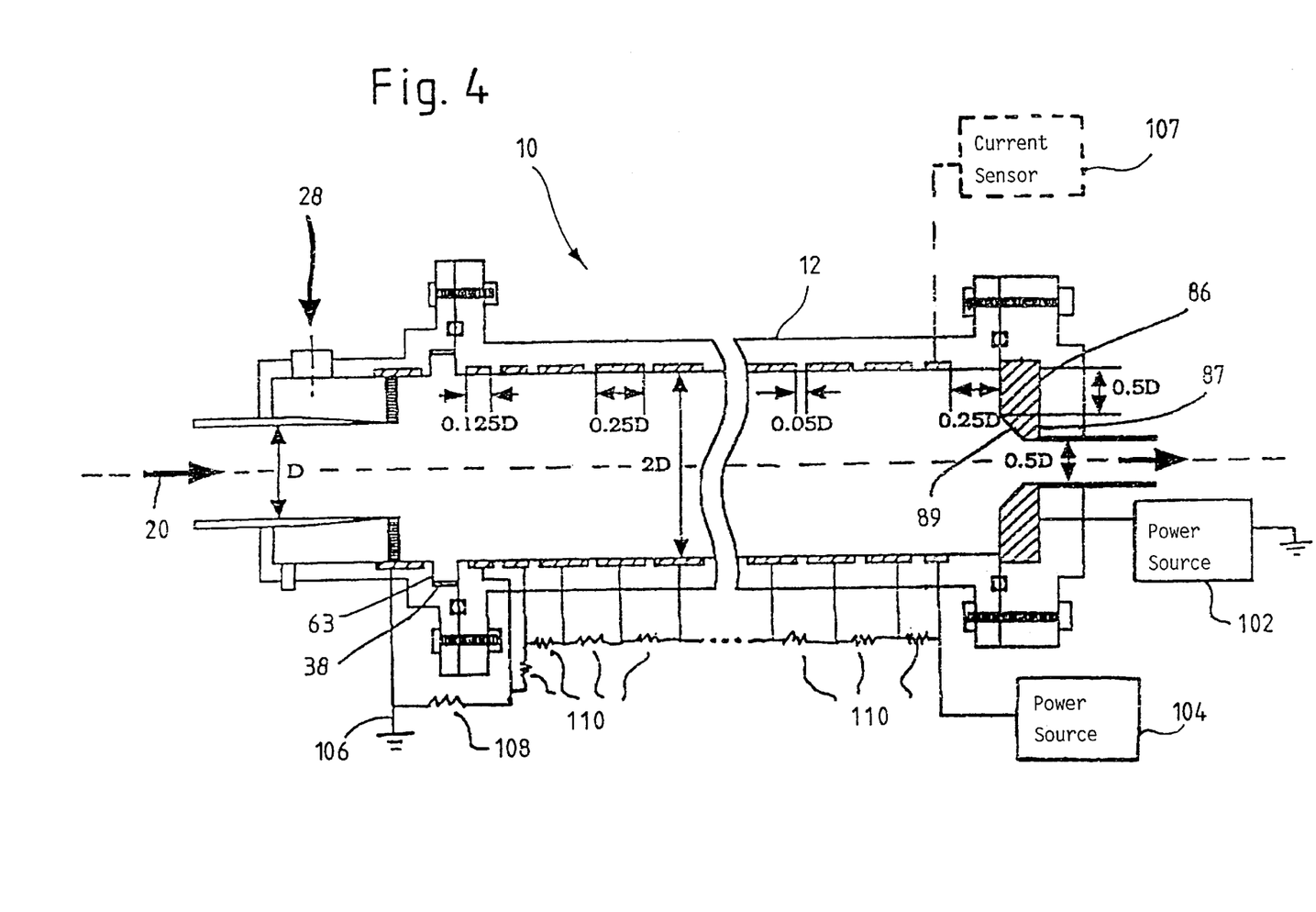
FIG. 4 is a more detailed cross-section illustration of the particle charging apparatus of FIG. 1 in accordance with the present invention.

One particular embodiment of a charging apparatus according to the present invention which is used in obtaining the results in the Example below is shown in FIG. 4. This embodiment includes more detail relative to the apparatus shown in FIG. 1 and uses the same reference numerals as used in FIG. 1 to designate the same or similar elements. The charging apparatus 10 as shown in FIG. 4 includes a ring electrode configuration 44 such as described with reference to FIG. 1. In this more detail illustration of the apparatus of FIG. 1, the voltages are applied to the various electrodes using two power sources 102, 104. The voltage ramp for the ring electrodes 46 is set up by placing resisters 110 between adjacent electrode rings 46 and a resistance 108 between ring electrode 48 and the ring electrode 98. The electrode 48 is connected to ground. A voltage is then applied to ring electrode 97 by power source 104 setting up the ramped voltages for the other electrodes 46. A separate power source 102 is provided to apply the voltage to the electrode 61 for reversing the electric field created by the ring electrode 46. However, one skilled in the art will recognize that any configuration which provides for a field having a reverse direction to that of the confined electric field may be used.

A preferred configuration for the electrode 61 is shown in FIG. 4. The electrode is a ring electrode including an inner ring portion 87 having an inner diameter of 0.5D and an outer diameter of 0.75D. The inner ring portion 87 is continuous with an outer ring portion 86 having an inner diameter of 0.75D and outer diameter of at least 1.0D. The inner ring portion 87 includes a 45 degree cut edge 89 facing the longitudinal axis. The thickness of the ring may vary, e.g., 0.5D.

In alternate configurations with respect to all the illustrative embodiments described herein, the power source for applying voltages to the various electrodes may be AC sources. When AC voltages are applied, an oscillating electric field is generated which can cause the charged particles to oscillate along the axis of the charger. This enables all the charged particles to attain the same residence time for charging and will result in a more uniform charge level on the particles.

Further, a current sensor 107 may be connected to an end electrode ring 98 of the apparatus 10 as shown in FIG. 4. The current sensor allows for the measurement of ion concentrations, N. The residence time, t, is the average length of time the charged particles reside in the charger which can be determined accurately by $V/(Q_a+Q_c)$, where V is the volume of the charger housing 12 and $Q_a$ and $Q_c$ are the aerosol and clean sheath air flow, respectively. The then known product (Nt) and the measured charge level can be used to test existing theories such as those described in the article by Fuchs, entitled "On the stationary charge distribution on aerosol particles in a bipolar ionic atmosphere," *Geodis:Pura.Appl.* Vol. 56, pp. 185–193 (1963); and the article by Hoppel and Frick, entitled "The nonequilibrium character of the aerosol charge distributions produced by neutralizer," *Aerosol Sci. & Technol.* Vol. 12, pp. 471–496. (1990).

Figure 6:
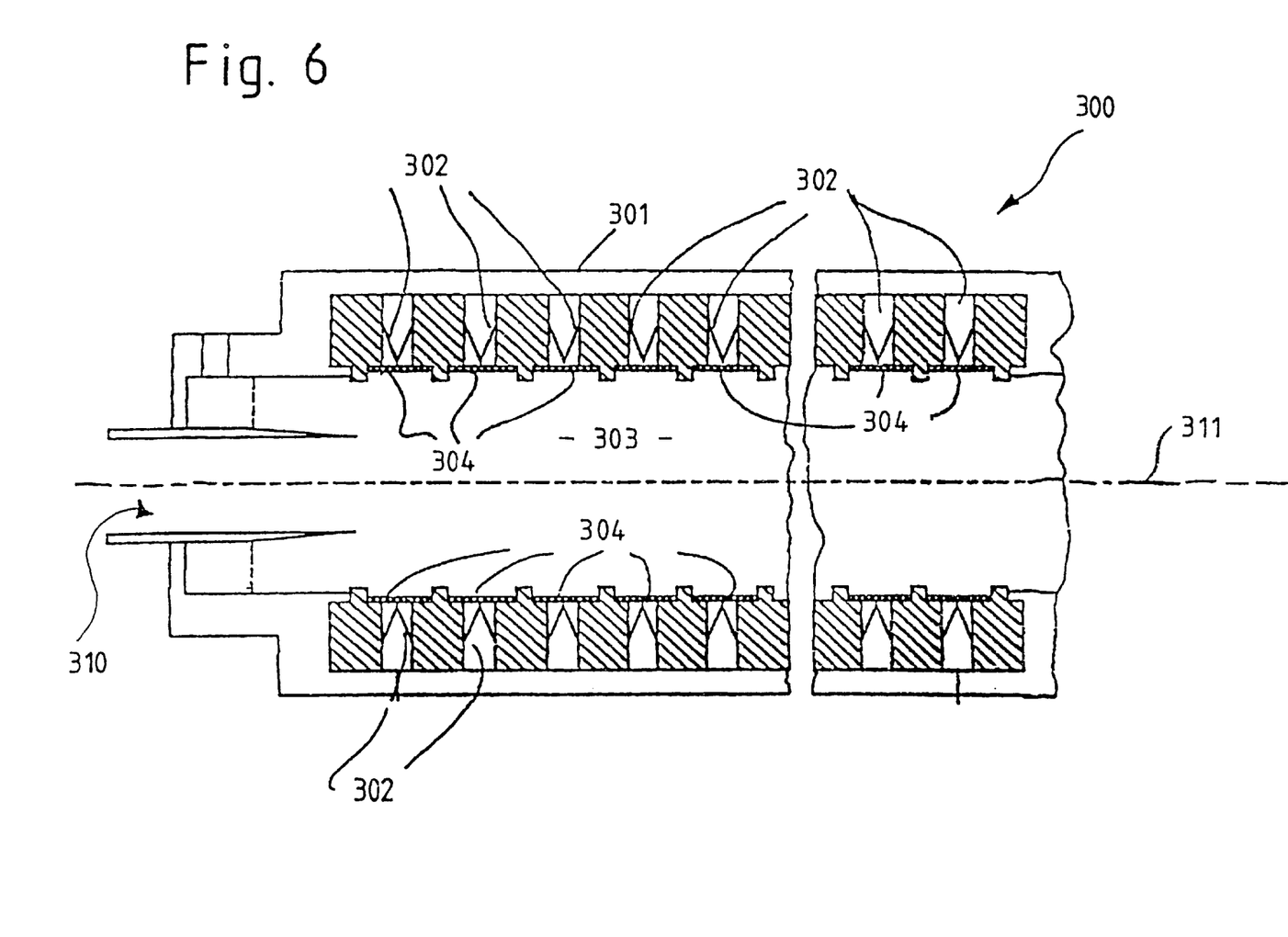
FIG. 6 is a further cross-section illustration of a portion of yet another alternate embodiment of the particle charging apparatus of FIG. 1 in accordance with the present invention.

In the alternate illustration of a portion of a charging apparatus 300 shown in FIG. 6 according to the present invention, the charger housing 301 defines the charging zone 303. Corona discharge rings or discs 302 having a sharpened edge are distributed along the housing 301 for providing free electrons and/or ions to the charging zone 303. The free electrons and/or ions are then used for charging the stream of aerosol particles flowing along the longitudinal axis 311 of the apparatus 300. The corona discharge rings or discs have a high voltage applied thereto (e.g., negative or positive). A plurality of perforated or porous metal plates or screens 304 are distributed along the housing 301 between the sharpened edges of the corona discharge discs and the charging zone 303. The perforated plates 304 allow the corona discharge to be formed about the sharpened edge with free electrons and/or ions being drawn into the charging region. The perforated plates 304 having ramped voltages applied thereto create the confined electric filed as described previously with respect to other embodiments herein, in addition to providing a lower reference voltage relative to the high voltage applied to the corona discharge elements for creation of the corona discharge. This embodiment provides for a high concentration of free electrons along the entire charging zone. Conventionally, as the mobility of free electrons is very high, it has been difficult to keep such free electrons "alive." With this configuration of corona discharge discs distributed along the longitudinal axis 311, a high concentration of free electrons is generated and kept alive throughout the entire charging zone 303.

EXAMPLE

An apparatus 10 as shown in FIG. 4 was used to determine particle penetration and charged fraction for various nominal particle diameters in the range of 1 nanometer to 100 nanometers. The voltage applied by the power source 104 was −1.5 kilovolts and the voltage applied by the power source 102 was −1.45 kilovolts. The resistor values for resistors 110 were 22 Megohms and the resistor value for resistor 108 was 44 Megohms. The aerosol flow 20 of silver particles classified by DMA was set at 1.5 liters/minute and the sheath air flow 28 was set at 4.5 liters/minute. The dimension (D) for the inlet diameter was 20 millimeters. The electrodes were stainless steel electrodes and the housing was plexiglass. The ion source 38 was four strips (1.8 cm by 0.5 cm) polonium-210 having a source strength of 0.5 mCi distributed in the annular slot 63.

Figure 7:
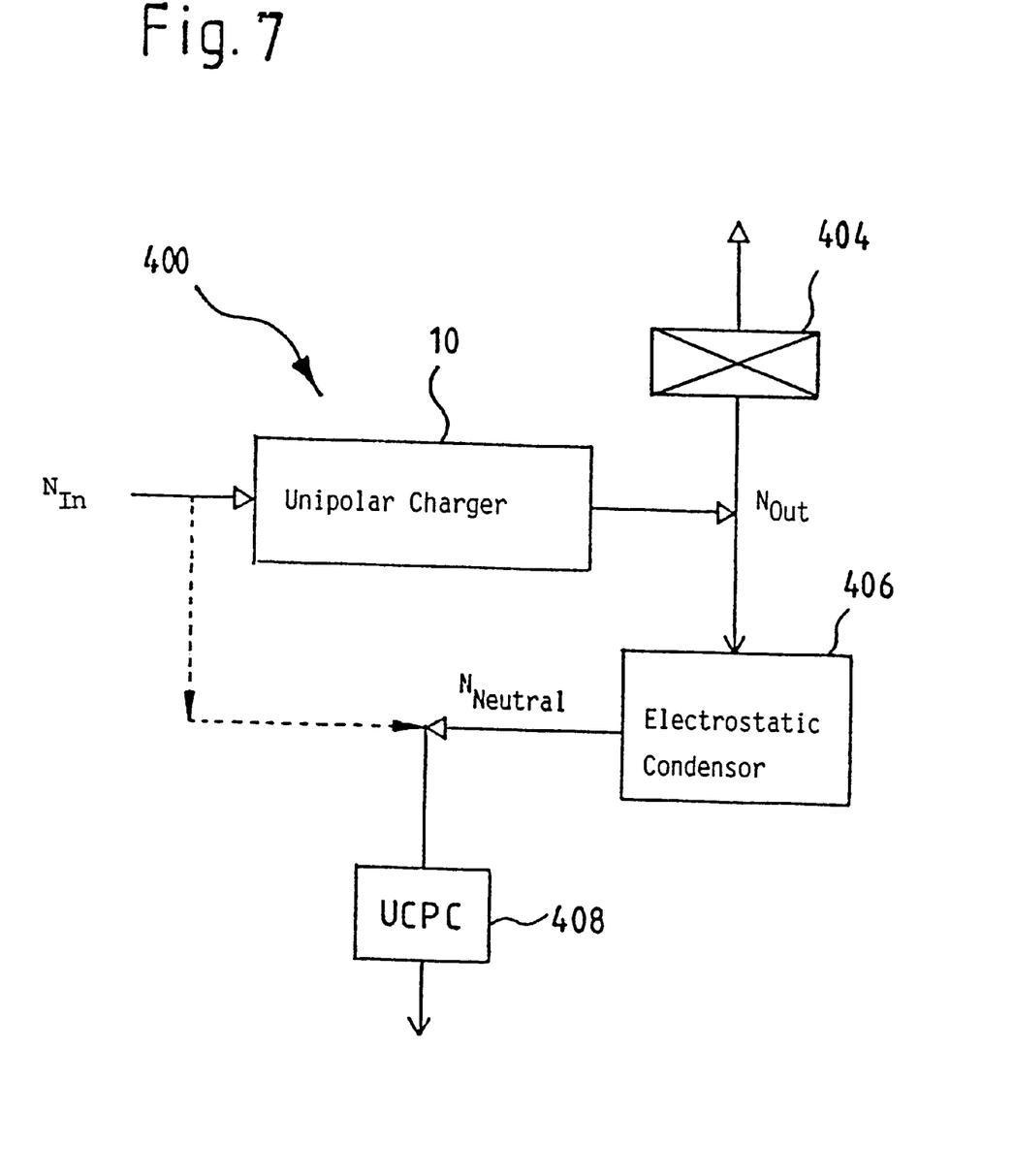
FIG. 7 is a block diagram of a setup for particle loss evaluation.

The test setup 400, as shown in FIG. 7, including the unipolar charger 10 as described above, further included electrostatic condenser 406 for removing charged particles from the concentration of particles $N_{out}$ resulting in concentration $N_{neutral}$. Both the flow of particles having a concentration $N_{in}$ and the flow having a concentration of $N_{neutral}$ are counted by a particle counter (TSI 3025A available form TSI, Inc.). Valve 404 provides a release for excess aerosol in the setup when desired.

Figure 9:
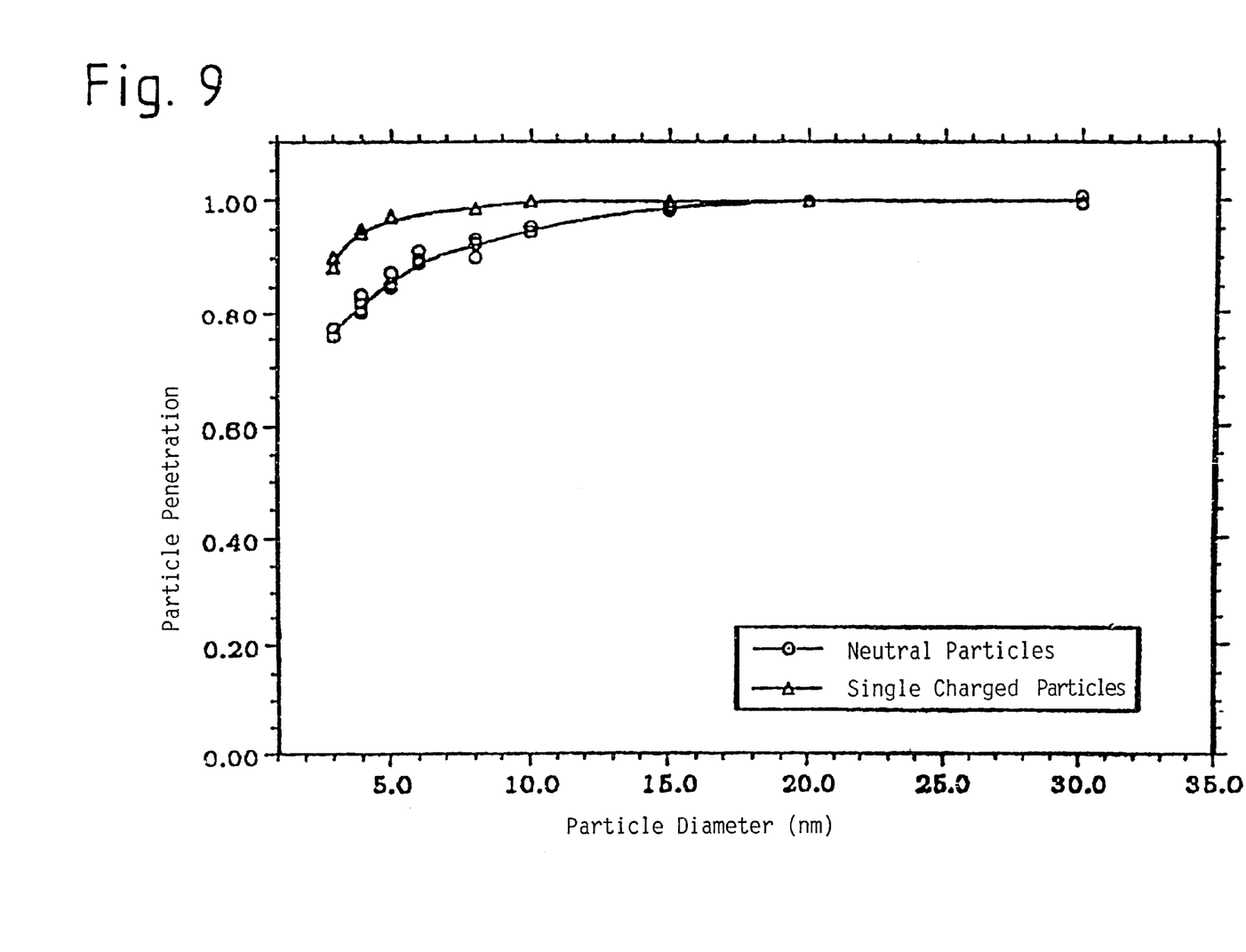
FIG. 9 is a graph showing particle penetration versus particle diameter using a particle charging apparatus in accordance with the present invention.

Particle penetration of neutral uniformly sized particles and singly charged uniformly sized particles as shown in FIG. 9 for various particle diameters is determined according to: Particle Penetration=$N_{out}/N_{in}$. To obtain the results shown in the graphs, the radioactive source is removed and neutral uniformly sized particles of a known mean diameter are introduced into the charger 10 with the all voltages off or on. The $N_{out}$ and $N_{in}$ for particles of this diameter were measured by particle counter 408 and particle penetration calculated. Likewise, the same was performed for singly charged particles introduced into the charger with all voltages on.

Charge fraction as shown in FIG. 9 for various particle diameters is determined according to: Charged Fraction=$1-N_{neutral}/N_{in}$. To obtain the results shown in the graphs, uniformly sized neutral silver particles of known mean diameter were introduced into the charger 10 with voltages turned on. $N_{in}$ (i.e., the neutral particle number before entering the charger with the charger on) for particles of a particular mean diameter were measured by particle counter 408. Thereafter, with the charger voltage on, $N_{neutral}$ (the neutral particle number after the electrostatic condenser 406 has removed the charged particles) is measured. The charged fraction is then calculated using these numbers.

As shown in the graph of FIG. 9, the particle penetration of a stream of neutral particles or singly charged particles having a nominal diameter as low as about 2 nanometers flowing through the charging apparatus 10 is greater than 60 percent. This indicates that the charging apparatus 10 has only small losses for uncharged particles or singly charged particles; such losses being less than 40 percent for nanometer particles having a diameter as low as 2 nanometers.

Figure 8:
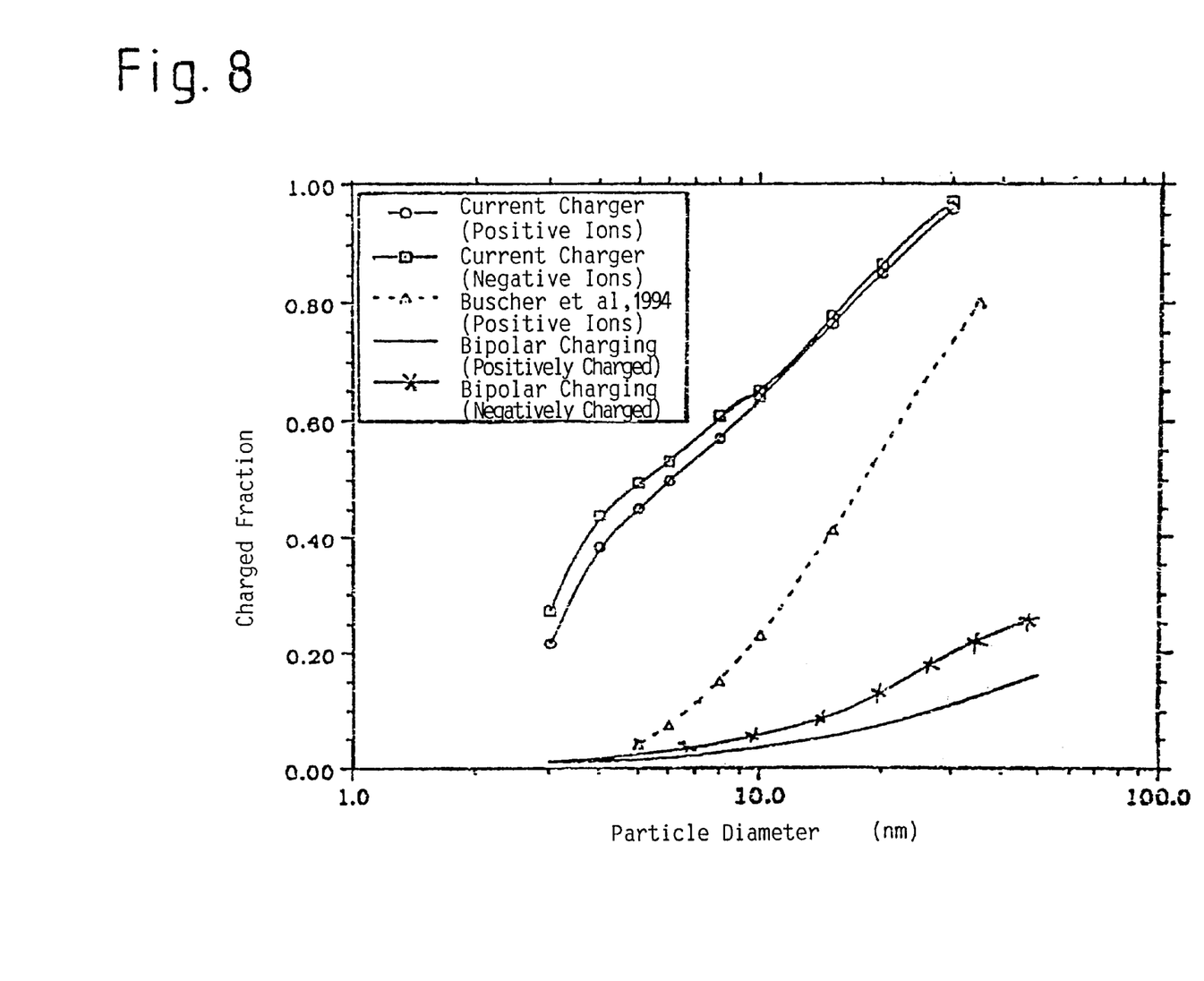
FIG. 8 is a graph of data showing charged fraction versus particle diameter resulting from an evaluation using the set up of FIG. 7 showing the advantages of the present invention over current state of the art chargers.

As shown in the graph of FIG. 8, the charged fraction for a stream of aerosol particles having particles with a nominal diameter as low as about 3 nanometers has a charged fraction exiting the charging apparatus greater than about 0.2. It is further shown that particles having a nominal diameter as low as about 4 nanometers exiting the charging apparatus 10 has a charged fraction greater than about 0.4; for particles having a nominal diameter as low as about 20 nanometers, the charged fraction is greater than about 0.8.

The results include data based on the charger 10 being operated with positive ions and negative ions (i.e., using the application of both positive voltages and negative voltages).

As shown in FIG. 8, charged fractions for particles having various diameters are also presented for a bipolar charging apparatus and an apparatus as described in Buscher, et al., entitled "Performance of a Unipolar 'Square Wave' Diffusion Charger With Variable nt-Product," *J.Aerosol.Sci*, Vol. 25, No. 4, pp. 651–663 (1994). As shown by the comparison data, the charging efficiency of the present charging apparatus 10 is approximately 10 to 100 times higher than the best available charger in the nominal diameter range of less than 10 nm.

All patents and references disclosed herein are incorporated by reference in their entirety, as if individually incorporated. Further, although the present invention has been described with particular reference to various embodiments thereof, variations and modifications of the present invention can be made within the contemplated scope of the following claims as is readily known to one skilled in the art.

What is claimed is:

1. A method for unipolar charging of aerosol particles, the method comprising the steps of:

providing a charger housing having a longitudinal axis extending between an inlet and an outlet of the charger housing with a stream of aerosol particles flowing parallel to the longitudinal axis from the inlet to the outlet; and creating a confined electric field within the housing parallel to the longitudinal axis for directing a stream of unipolar ions to flow parallel to the longitudinal axis of the charger housing towards the outlet for use in charging the stream of aerosol particles.

2. The method according to claim 1, wherein the method further includes creating a clean sheath between the stream of aerosol particles and the charger housing.

3. The method according to claim 1, wherein the step of creating the confined uniform electric field within the housing includes the steps of:

positioning a plurality of ring electrodes along the longitudinal axis; and applying a plurality of voltages ramped in level from a first ring electrode to a last ring electrode of the plurality of ring electrodes lying along the longitudinal axis.

4. The method according to claim 3, wherein the step of applying the plurality of voltages includes the steps of:

connecting a resistance between adjacent rings of the plurality of rings;

applying a voltage to the first ring electrode; and grounding the last ring electrode.

5. The method according to claim 3, wherein the plurality of voltages are DC voltages.

6. The method according to claim 3, wherein the plurality of voltages are AC voltages.

7. The method according to claim 1, wherein the charger housing includes a nonconducting tubular portion having an inner surface, and further wherein the step of creating the confined uniform electric field within the housing includes the steps of:

providing a layer of resistive material having a first end and a second end, the layer of resistive material extending along a length of the inner surface of the nonconducting tubular portion;

applying a voltage to the first end; and grounding the second end.

8. The method according to claim 7, wherein the voltage is a DC voltage.

9. The method according to claim 7, wherein the voltage is an AC voltage.

10. The method according to claim 1, wherein the stream of unipolar ions is provided by positioning a radioactive source in proximity to the inlet of the charger housing to generate bipolar ions, wherein the confined electric field pushes ions of one polarity towards the inlet and allows the stream of unipolar ions to be directed in a flow parallel to the longitudinal axis of the charger housing towards the outlet.

11. The method according to claim 1, wherein the stream of unipolar ions is provided by one or more corona discharge electrodes having a voltage applied thereto.

12. The method according to claim 1, wherein the method further comprises the step of creating an outlet electric field proximate the outlet of the charger housing, the outlet electric field having a direction generally opposite of the direction of the confined electric field such that charged particles are forced towards the longitudinal axis.

13. The method according to claim 12, wherein the method further comprises the step of sizing the charger housing such that the stream of aerosol is contracted proximate the outlet of the charger housing such that charged particles of the stream are forced towards the longitudinal axis.

14. The method according to claim 1, wherein the charger housing defines an obstruction free open space extending from the inlet to the outlet.

15. An aerosol particle charging apparatus for use in charging a stream of aerosol particles, the apparatus comprising:

an elongated charger housing having a longitudinal axis extending between an inlet and an outlet defined therein, the inlet for receiving the stream of aerosol particles and the outlet for allowing the stream of aerosol particles to exit the charger housing; and an electrode configuration operable to create a confined uniform electric field within the housing parallel to the longitudinal axis for use in directing a stream of unipolar ions to flow parallel to the longitudinal axis of the charger housing towards the outlet.

16. The apparatus according to claim 15, wherein the apparatus further includes means for creating a clean sheath between the stream of aerosol particles and the charger housing.

17. The apparatus according to claim 15, wherein the elongated charger housing includes an annular housing having an inlet end and an outlet end with the longitudinal axis extending therethrough, and further wherein the apparatus includes an annular inlet member at the inlet end of the annular housing sized to provide the stream of aerosol particles to a charging zone defined in the annular housing, the apparatus further includes a gas inlet cavity defined between the annular housing and the annular inlet member for receiving a gas and directing the gas between the stream of aerosol particles flowing parallel to the longitudinal axis and the annular housing.

18. The apparatus according to claim 15, wherein the electrode configuration includes:

a plurality of ring electrodes located along the longitudinal axis; and one or more power sources for use in applying a plurality of voltages ramped in level from a first ring electrode to a last ring electrode of the plurality of ring electrodes lying along the longitudinal axis.

19. The apparatus according to claim 18, wherein adjacent rings of the plurality of rings are electrically connected with a resistance therebetween, and further wherein the one or more power sources are connected for applying a voltage to the first ring electrode with the last ring electrode grounded.

20. The apparatus according to claim 19, wherein the power sources are DC voltage sources.

21. The apparatus according to claim 19, wherein the power sources are AC voltage sources.

22. The apparatus according to claim 15, wherein the elongated charger housing includes a nonconducting tube portion having an inner surface, and further wherein the electrode configuration includes a layer of resistive material having a first end and a second end located along a length of the inner surface of the nonconducting tube portion, the one or more power sources are connected for use in applying a voltage to the first end with the second end grounded.

23. The apparatus according to claim 15, wherein the apparatus further includes an ion source positioned in proximity to the inlet of the charger housing along an inner surface of the charger housing to generate bipolar ions, an electrode is positioned between the inlet of the charger housing and the ion source such that the confined electric field pushes ions of one polarity towards the electrode allowing the stream of unipolar ions to be directed to flow parallel to the longitudinal axis of the charger housing.

24. The apparatus according to claim 15, wherein the apparatus further includes one or more corona discharge electrodes for use in providing the stream of unipolar ions.

25. The apparatus according to claim 15, wherein the elongated charger housing includes an annular housing having an inlet end and an outlet end with the longitudinal axis extending therethrough, and further wherein the apparatus includes an annular inlet member at the inlet end and an annular outlet member at the outlet end, the annular outlet member has a diameter less than a diameter of the annular inlet member such that the stream of aerosol particles is contracted proximate the outlet of the charger housing forcing the stream of aerosol particles towards the longitudinal axis of the charging device.

26. The apparatus according to claim 15, wherein the apparatus further comprises an electrode proximate the outlet of the charger housing operable to create an outlet electric field in a direction generally opposite of the direction of the confined electric field such that charged particles of the stream of aerosol particles are forced towards the longitudinal axis.

27. The apparatus according to claim 15, wherein the charger housing defines a substantially obstruction free charging zone extending from the inlet to the outlet.

28. An aerosol particle charging apparatus for use in charging a stream of aerosol particles, the apparatus comprising:

an elongated charger housing having a longitudinal axis extending between an inlet and an outlet defined therein, the inlet for receiving the stream of aerosol particles and the outlet for allowing the stream of aerosol particles to exit the charger housing;

means for creating a confined electric field within the housing parallel to the longitudinal axis for use in directing a stream of unipolar ions to flow parallel to the axis of the charger housing; and means for creating a clean sheath between the stream of aerosol particles and the charger housing.

29. The apparatus according to claim 28, further comprising means for creating an outlet electric field in a direction generally opposite of the confined electric field such that charged particles of the stream of aerosol particles are forced towards the longitudinal axis.

30. The apparatus according to claim 28, wherein the charger housing includes means for contracting the stream of aerosol particles proximate the outlet of the charger housing forcing the stream of aerosol particles towards the longitudinal axis of the charging apparatus.

31. An aerosol particle charging apparatus for use in charging a stream of aerosol particles, the apparatus comprising:

an elongated charger housing having a longitudinal axis extending between an inlet and an outlet defined therein, the inlet for receiving the stream of aerosol particles and the outlet for allowing the stream of aerosol particles to exit the charger housing, wherein the charger housing includes means for contracting the stream of aerosol particles proximate the outlet of the charger housing forcing the aerosol particles towards the longitudinal axis;

means for creating a confined electric field within the housing parallel to the longitudinal axis for use in directing a stream of unipolar ions to flow parallel to the axis of the charger housing towards the outlet; and means for creating an outlet electric field in a direction generally opposite of the confined electric field such that charged particles of the stream of aerosol particles are forced towards the longitudinal axis.

32. An aerosol particle charging apparatus for use in charging a stream of aerosol particles, the apparatus comprising:

an elongated charger housing having a longitudinal axis extending between an inlet and an outlet defined therein, the inlet for receiving the stream of aerosol particles and the outlet for allowing the stream of aerosol particles to exit the charger housing;

a plurality of corona discharge elements positioned along the longitudinal axis for providing free electrons/ions into a charging zone defined by the charger housing; and an electrode configuration operable to create a confined uniform electric field within the housing parallel to the longitudinal axis for use in directing the free electrons/ions to flow parallel to the axis of the charger housing towards the outlet.

33. The apparatus according to claim 32, wherein the corona discharge elements include a plurality of sharpened edge disc elements and the electrode configuration includes a plurality of screen elements positioned between the sharpened edge of the corona discharge elements and the charging zone.

* * * * *